United States Patent [19]

Gray et al.

[11] Patent Number: 4,870,970

[45] Date of Patent: Oct. 3, 1989

[54] ULTRASONIC INVESTIGATION APPARATUS

[75] Inventors: Nigel Gray; Simon Knibbs; Patrick A. Finlay; Robert L. Crocker, all of Slough, Great Britain

[73] Assignee: Fulmer Limited, Bucks, United Kingdom

[21] Appl. No.: 190,689

[22] PCT Filed: Aug. 12, 1987

[86] PCT No.: PCT/GB87/00570

§ 371 Date: May 6, 1988

§ 102(e) Date: May 6, 1988

[87] PCT Pub. No.: WO88/01151

PCT Pub. Date: Feb. 25, 1988

[30] Foreign Application Priority Data

Aug. 12, 1986 [GB] United Kingdom ............... 8619579

[51] Int. Cl.⁴ ............................................. A61B 8/00
[52] U.S. Cl. .............................. 128/660.09; 128/915; 73/620
[58] Field of Search ......... 128/660.01, 660.07–660.10, 128/662.06; 73/644, 620

[56] References Cited

U.S. PATENT DOCUMENTS

| | | | |
|---|---|---|---|
| 3,480,002 | 11/1969 | Flaherty et al. | 128/660.09 |
| 3,854,471 | 12/1974 | Wild | 128/915 X |
| 4,059,098 | 11/1977 | Murdock | 73/644 X |
| 4,099,420 | 7/1978 | Stouffer et al. | 73/629 |
| 4,105,018 | 8/1978 | Greenleaf et al. | 128/2 V |
| 4,275,597 | 6/1981 | Quedens et al. | 128/663.01 X |
| 4,398,425 | 8/1983 | Matzuk | 73/633 |
| 4,433,690 | 2/1984 | Green et al. | 128/915 X |
| 4,545,385 | 10/1985 | Pirschel | 128/915 X |
| 4,572,202 | 2/1986 | Thomenius | 128/660 |
| 4,681,120 | 6/1987 | Kunii | 128/915 X |

FOREIGN PATENT DOCUMENTS

| | | |
|---|---|---|
| 0018771 | 4/1980 | European Pat. Off. . |
| 0032129 | 1/1981 | European Pat. Off. . |
| 2294433 | 12/1974 | France . |
| 2015732 | 2/1979 | United Kingdom . |

OTHER PUBLICATIONS

Benthin, Metal "Apparatus for Displaying Reflected UTGS Pulses", Intnl Appln (PCT) WO82/04183 publ. 12/1982.

Chow, C. K. et al "Dig. Processor for Data Compaction and Image Enhancement of Echographic Signals", IBM Technical Disclosure Bulletin vol. 17, No. 10, pp. 3154–3158, Mar. 1975.

Taylor, W. B. et al "A High-Resolution Transrectal UTS System", UTS in Med & Biol. vol. 5, pp. 129–138.

*Primary Examiner*—Francis Jaworski
*Attorney, Agent, or Firm*—Parmelee, Miller, Welsh & Kratz

[57] ABSTRACT

An apparatus for transmitting acoustic ultrasonic pulses and for receiving "echos" of the transmitted pulses, comprises a housing, an upstanding wall mounted on the housing defining the mouth of a well, and a transducer mounted in the housing so that the operative part of the transducer is located in the well. The well is substantially watertight and is provided with a jet for introducing water or other fluids to the well, or is prefilled with fluid.

12 Claims, 3 Drawing Sheets

ULTRASONIC INVESTIGATION APPARATUS

The present invention relates to an ultrasonic investigation apparatus more particularly relates to a skin investigation apparatus for use with an ultrasonic investigation technique.

It has been common practice, in recent years, to carry out investigations of the human body and other animal bodies utilising ultrasonic techniques. In carrying out investigations in this way an ultrasonic transducer has been accoustically coupled to the skin of a patient, for example by pressing the transducer to the skin of the patient which may be lubricated with an appropriated coupling medium, and then exciting the transducer. Ultrasonic pulses are then transmitted into the patient and are reflected from reflecting surfaces within the patient. The reflected pulses are received by the transducer, generating signals representative of the pulses, and these signals may be processed by appropriate processing machinery to enable a visual representation of the part of the patient under examination to be created.

Examination techniques of this type are widely utilised, for example, in the examination of a developing foetus in the womb of a pregnant mother.

Ultrasonic pulses transmitted into the body are partially reflected at each interface that they pass within the body. Thus the ultrasonic pulses are reflected by the various interfaces between the layers constituting the outermost surface of the body, that is to say the skin.

Usually the skin of the human body has an outermost layer consisting of an epidermis, and lying immediately beneath the epidermis is the dermis. Typically the dermis extends to a depth 2 mm from the outermost surface of the body. Under that lies subcutaneous fat, and the thickness of the subcutaneous fat depends upon the physiology of the patient, and the particular part of the body being considered. Under the subcutaneous fat lies the muscle.

It is desirable to be able to investigate the precise structure of the skin, in order to assist in the diagnosis of various diseases, such as skin cancer, and also in order to be able to locate accurately the positions of scars and burns, since this may well assist in connection with remedial plastic surgery.

According to one aspect of this invention there is provided an apparatus for transmitting accoustic ultrasonic pulses and for receiving "echos" of the transmitted pulses, said apparatus comprising a housing, an upstanding wall mounted on the housing defining the mouth of a well, a transducer mounted in the housing so that the operative part of the transducer is located in the well, the well being substantially watertight and being provided with means for introducing water or other fluids to the well, or being pre-filled with fluid.

According to another aspect of this invention there is provided an apparatus for transmitting accoustic ultrasonic pulses and for receiving "echos" of the transmitted pulses, said apparatus comprising a housing, an upstanding wall mounted on the housing defining the mouth of a well, a transducer mounted in the housing so that the operative part of the transducer is located in the well, the transducer being controllably movable within the well, the well being substantially watertight and being provided with means for introducing water or other fluid to the well or being pre-filled with fluid.

Preferably the well is provided with means for introducing fluid to the well in the form of a pump and a conduit to direct fluid from the pump into the well.

Conveniently the well is provided with a sealable bore in a wall thereof to permit fluid to be introduced to the well.

Preferably means are provided for withdrawing fluid from the well.

Conveniently the well is sealed at the mouth by a flexible membrane.

Advantageously there is a space between the membrane and the top of the wall defining the mouth of the well.

Conveniently the transducer is mounted in a movable housing, a flexible lower membrane being sealingly connected to the said wall defining the well and being sealingly connected to part of the movable housing.

Preferably said lower membrane is sealingly connected to the upstanding wall by means of a sealing ring received in an annular recess formed in the wall, the sealing ring sealingly trapping the said membrane.

Conveniently said lower membrane is sealingly connected to an upstanding part of the movable housing mounting the transducer, by means of a sealing ring.

Preferably the transducer is mounted in a vertical bore formed in the movable housing accommodating the transducer, the transducer being sealed by at least one sealing ring mounted between the wall defining the bore and the transducer.

Advantageously the housing accommodating the transducer is mounted for movement on linear bearings.

Preferably an electric motor is provided adapted to drive a threaded rod which passes through a threaded aperture formed in part of the housing accommodating the transducer, actuation of the motor causing rotation of the threaded rod, thus driving the housing accommodating the transducer.

Conveniently limit switch means are provided for detecting predetermined limit positions of the housing mounting the transducer.

The limit switch means may comprise a microswitch cooperating with a cam surface formed or mounted on the movable housing mounting the transducer, or proximity switches of the Hall effect type, or optical switching means.

Means may be provided for moving the transducer, within the well, in two orthogonal directions, and/or towards or away from the surface of the well, and/or for pivoting the transducer within the well.

According to another aspect of this invention there is provided a method of investigating an article with ultrasonic pulses, said method comprising the steps of utilising a transmitter/receiver assembly.

According to another aspect of this invention there is provided an ultrasonic investigation apparatus, said apparatus comprising a pulse generator, a transducer assembly driven by the pulse generator adapted to transmit an accoustic pulse and receive echos of the accoustic pulse, a real time analogue to digital convertor to convert pulses received from the transducer, and calculating means adapted to calculate from the digitised signals the configuration of an item under investigation.

Preferably the analogue to digital convertor converts an echo signal into 1024 pixels with eight bit precision, the digitised signal being transferred to a computer by means of a bus.

In order that the invention may be more readily understood, and so that further features thereof may be appreciated, the invention will now be described, by way of example, with reference to the accompanying drawings in which.

Figure 1:
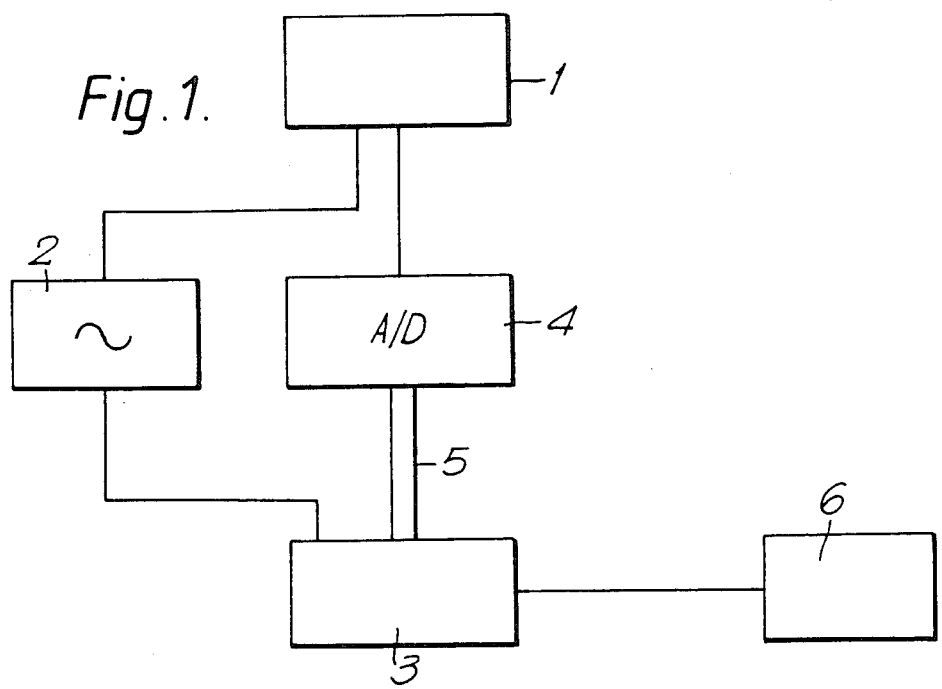
FIG. 1 is a schematic block diagram of an arrangement in accordance with the invention.

Referring initially to FIG. 1 of the accompanying drawings an apparatus in accordance with the invention comprises an ultrasonic pulse transmitting and receiving assembly 1, which will be described hereinafter in greater detail. The assembly incorporates a PVDF transducer which is mounted in such a way that the transducer can be accoustically coupled to the skin of a patient.

The transmitter and receiver assembly 1 is connected to receive pulses from a pulse generator 2, the pulse generator generating pulses of a frequency between 30 and 50 MHz. The pulse generator is controlled by a computer 3. The transmitter and receiver 1 is adapted to transmit the pulse from the pulse generator as an accoustic pulse, and to receive the "echos" of the accoustic pulse from the patient. The received signals are transmitted to an analogue to digital convertor 4, which converts the received signal into 1024 pixels with eight bit precision. The analogue to digital convertor is thus able to convert the received "echo" in real time, and the digitised signal is then rapidly transverted to computer 3 by means of an IEEE 488 bus 5. Within the computer the signal is rectified, and is passed through a low pass filter in order to distinguish the "echos" present in the echo signal. The signal can be further processed within the computer.

The transducer present in the receiver and transmitter 1 may be moved relative to the skin of the patient, that is to say it may be scanned, and this scanning enables a two-dimensional representation to be generated by the computer for display on an appropriate display device 6, such as a colour monitor, and thus the apparatus may generate and display a two-dimensional representation of the skin of a patient.

The transmitter and receiver assembly 1 must, as will be appreciated from the foregoing description, consist of an transducer which can be accoustically coupled to the skin of a patient, but which can be accurately indexed or scanned relative to the patient.

Figure 2:
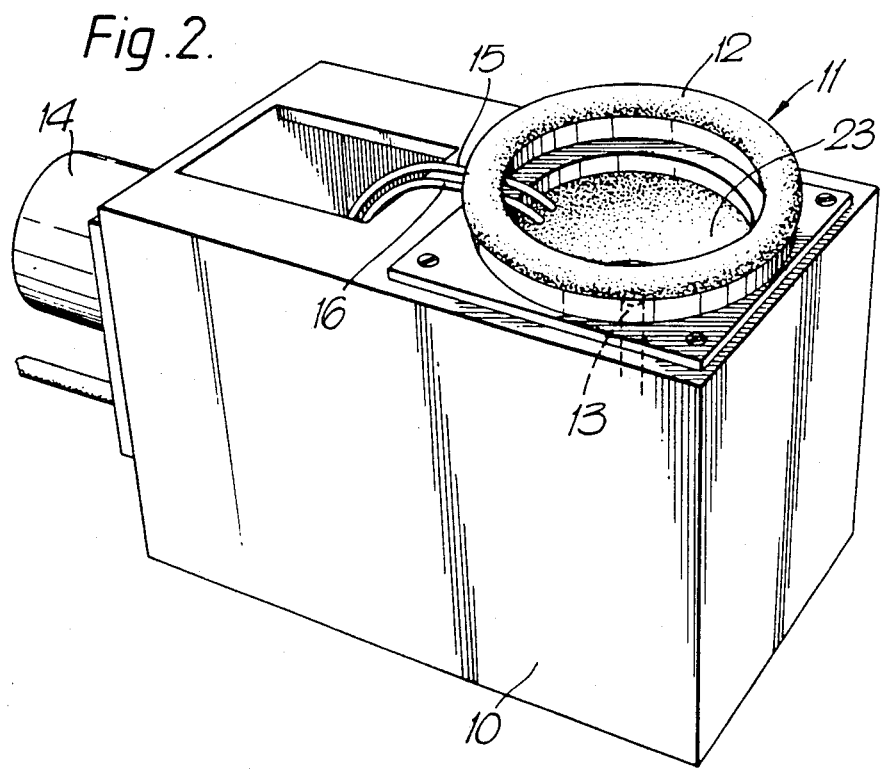
FIG. 2 is a perspective view of a sensor head apparatus in accordance with the invention.

FIG. 2 is an illustrative view of a pulse transmitting and receiving transducer assembly which consists of a main housing 10, on the upper surface of which is mounted a well 11. The well 11 is effectively defined by an upstanding wall 12, defining, in the illustrated embodiment, an oval recess. The lower part of the recess is, as will be described hereinafter, sealed in a watertight manner, and is provided with a transducer 13 which can be moved axially within the well, by means of a motor 14. Two conduits 15, 16 are provided which communicate with the interior of the well. Water may be injected into the well through the conduit 16 and may be withdrawn from the well through the conduit 15.

In utilising the assembly as shown in FIG. 2 the portion of the skin of a patient to be investigated is brought into contact with the top surface of the wall 12 that defines the well 11. Water can then be injected into the well through the conduit 16, until the water touches the skin of the patient. At this stage some water may escape between the upper surface of the wall 12 of the well and the skin of the patient, but this ensures that no air bubbles remain within the well. If the transducer is then energised, the ultrasonic accoustic pulses generated by the transducer will be coupled, by the water, into the skin of the patient and equally any "echos" reflected by the interfaces present in the skin layers of the patient will again be coupled to the transducer by the water. The transducer may be indexed, within the well, as will be described hereinafter, thus enabling the described apparatus to be located in position on a patient, and to then perform an operational cycle in which the transducer is indexed or scanned between selected positions, the transducer transmitting ultrasonic pulses and receiving the corresponding "echo" pulses whilst at that location. The entire procedure is computer controlled, and the computer is able, as has been mentioned above, to generate a two-dimensional representation of the area of the skin of the patient undergoing the investigation.

When the investigation cycle is complete the water may be withdrawn from the well 11 through the conduit 15, and the apparatus is then ready for re-use.

Whilst the apparatus has been shown in FIG. 2 in one orientation, it is to be appreciated that the apparatus may be brought into contact with any part of the skin of the patient, in any orientation, and then the well 11 may be filled by introducing water into the well through the conduit 16.

Figure 3:
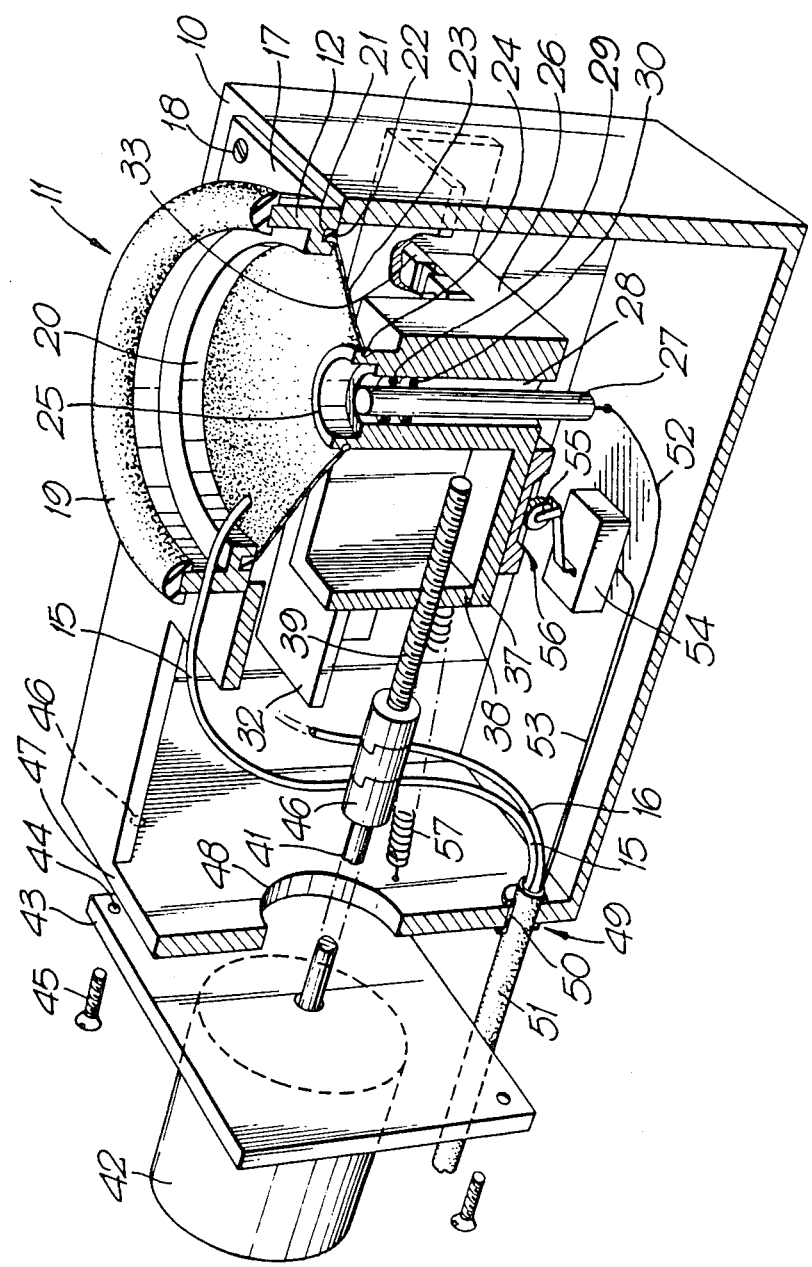
FIG. 3 is a part-sectional part-cut-away view of the apparatus shown in FIG. 2, the section being a longitudinal section.

Turning now to FIG. 3 of the accompanying drawings it can be observed that the well 11 is defined by an upstanding wall 12 which is formed integrally with a plate 17 which is screwed by means of screws 18 to the main housing 10.

The upper part of the upstanding wall 12 is provided with an elastomeric cover 19 to ensure that comfortable contact between the wall 12 and a patient can be established.

The conduit 15 is shown passing through an aperture formed in the upstanding wall 12, so that communication is established with the interior of the well 11, and the conduit 16 may pass through a corresponding aperture. The conduit 15 is preferably mounted to direct a stream of water directly at the transducer.

The lower part of the wall 12 is provided with radially inwardly directed flange 20, the undersurface of which is provided with a recess 21, which is of annular form and is adapted to receive an O-ring 22. The O-ring acts to trap, within the annular recess 21, the upper part of a tubular flexible thin rubber membrane 23. The membrane 23 forms a flexible bottom to the well 11, and may be termed a lower membrane.

The lower part of the flexible membrane is secured by means of a further O-ring 24 to the exterior surface of an upstanding collar 25 formed integrally with a housing 26 in which a transducer 27 is mounted. The housing 26 defines a vertical cylindrical bore 28, formed concentrically with the collar 25, the bore terminating within the collar 25. The transducer 27, which is of cylindrical configuration, is mounted within the bore 26, and two O-rings 29, 30 are located between the transducer and the wall defining the bore 28, to form a watertight seal.

It can thus be seen that the described components constitute a substantially watertight well, the wall 12 being formed integrally, and the flexible rubber membrane being sealed to the flange 20 formed integrally with the wall 11 by means of a sealing ring 21 and also being sealed to the collar 25 by means of a sealing ring 24. A space between the wall of the bore 28 and the transducer is sealed by means of the sealing rings 29, 30.

Figure 4:
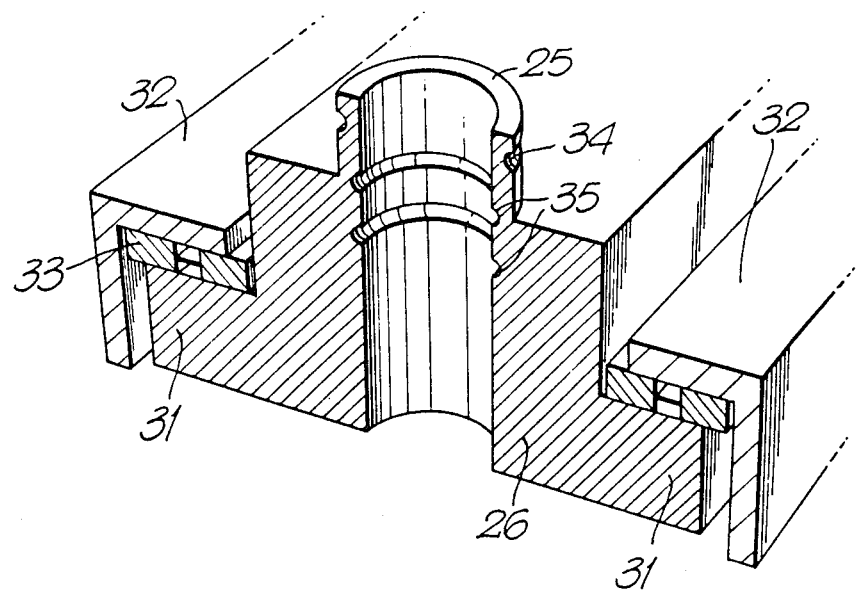
FIG. 4 is a transverse sectional view of part of the apparatus shown in FIG. 3.

The housing 26 is mounted in such a way that it can slide axially of the housing 10. As can be seen in FIG. 4, the housing 26 is provided with two laterally projecting flanges 31, which co-operate with inwardly directed flanges 32 mounted on the longitudinal side walls of the housing 10. Located between the cooperating flanges is a linear bearing 33 and the arrangement is such that the components are retained in the relative position illustrated but the housing 26 may move axially.

As the housing 26 moves axially, so the flexible rubber membrane 23 will flex, maintaining the well 11 in a watertight condition, but permitting movement of the transducer assembly within the well.

As can be seen from FIG. 4 the housing 26 is provided with grooves 34, 35, 36 to receive the O-rings 24, 29, 30 mentioned above.

The housing 26 in which the transducer is mounted is provided with a projecting portion 37 which defines a transversely extending wall 38 provided with a threaded bore which receives a threaded rod 39. The threaded rod is coupled, by means of a part flexible coupling 40 to the drive shaft 41 of an electric motor 42. The electic motor is provided with an integral mounting plate 43 provided with apertures 44 through which screws 45 may be inserted to engage with appropriately provided apertures 46 present in a transverse wall 47 formed integrally with the housing 10. The wall 47 is provided with an aperture 48 to accommodate the drive shaft 41 of the motor 42.

The transverse wall 47 is also provided with an appropriate inlet port 49 illustrated as being provided with a grommet 50 to receive an input tube 51 which contains the water supply and drain conduits 15 and 16, and an electric lead 52 leading to the transducer 27 and a further electric lead 53 which extends to a microswitch 54 the operating arm 55 of which engages a cam recess 56 formed on the undersurface of the housing 26. An appropriate electric lead is also provided (not shown) connected to the electric motor 42.

A spring 57 may be provided extending between the transverse wall 47 and the housing 26 to provide a bias to the housing 26 tending to draw the housing 26 towards the wall 47.

In operation of the device the conduits 15 and 16 may be utilised to fill and empty the well as described above. The motor 42 may be actuated, under the control of the computer, to rotate the threaded rod 39, thus driving the housing 26 axially. When the housing 26 reaches a limit position the cam 56 actuates the microswitch 54. The direction of rotation of the motor may then be reversed, thus causing the housing 26 to move to the other limit position.

Whilst one embodiment of the invention has been described many modifications may be effected without departing from the scope of the invention. Whilst of course other drive arrangements and bearing means may be utilised it is envisaged that instead of utilising a microswitch of the type described, the limit positions of the movable housing 26 may be detected by means of an optical arrangement, or by means of Hall effect switches or other proximity sensing switches.

Whilst the invention has been described with reference to a relatively simple embodiment in which the transducer is mounted for axial movement relative to the well, it is envisaged that it may be preferable to provide embodiments in which the transducer is not only movable axially of the well, but is also movable transversely to the well. It is thus envisaged that a further drive motor may be provided adapted to move the transducer assembly in a transverse direction. It is envisaged that it may also prove desirable to be able to move the transducer itself towards and away from the surface of water present in the well, and thus means may be provided to move the transducer, in the orientation shown in FIG. 3, in a vertical direction. Alternatively again it may be desirable to be able to tilt or pivot the transducer relative to the surface of the well, and again it is envisaged that means may be provided to perform this function.

Figure 5:
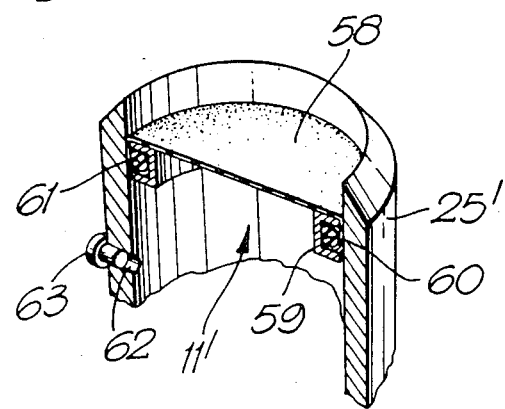
FIG. 5 is a sectional view of part of a modified embodiment of the invention.

In an alternative embodiment of the invention, part of which is shown in FIG. 5, the open mouth of a collar 25′, which defines a well 11′ containing a transducer arrangement as described above is provided with a thin flexible sealing membrane 58, such as a thin rubber membrane. The membrane 58 is stretched over a support ring 59 which has an annular groove 60 in its outer peripheral surface, and is sealingly trapped by a resilient O-ring 61 which is in the groove 60. The combination of the membrane 58 and support ring 59 is a sealing friction fit in the open mouth of the well. A bore 62 is provided through the wall of the well to enable the well to be filled, with an acoustic coupling fluid, such as water, and the bore may be sealed with a plug 63. In use of this embodiment an acoustic coupling gel is inserted in the space between the membrane 58 and the top of the well and the device is then used in a manner corresponding to that described above. This embodiment is easier to use, since the well does not need to be filled before an image is obtained. Also the device can be more easily utilised in positions where the open mouth of the well is directed downwardly. The well may, of course, be pre-filled with fluid and permanently sealed.

Whilst the invention has been described with reference to a proposed medical ultrasonic investigation it is to be appreciated that the apparatus of the invention may be utilised in carrying out ultrasonic investigations of inanimate objects, as well as in carrying out ultrasonic investigations of living patients.

We claim:

1. An apparatus for transmitting acoustic ultrasonic pulses and for receiving "echos" of the transmitted pulses, said apparatus comprising a first housing, an upstanding wall mounted on the housing defining the mouth of a well, the well having an upper region adjacent the mouth and a lower region, a transducer located in the first housing so that the operative part of the transducer is located in the well, the transducer being mounted in a moveable housing which is moveable linearly relative to said upstanding walls and which is provided with controllable means to move the housing, a flexible membrane being provided in the lower region of the well and being sealingly connected to the said wall defining the well and being sealingly connected to part of the moveable housing so that the membrane forms the bottom of the well, the well being substantially water-tight and being provided with means for introducing water or other fluids to the well, or being pre-filled with fluid, the means to move the housing engaging the housing at a point separated from said well by said membrane.

2. An apparatus according to claim 1 wherein the well is provided with said means for introducing fluid to the well in the form of a pump and a conduit to direct fluid from the pump into the well.

3. An apparatus according to claim 1 wherein the well is pre-filled with fluid and wherein the well is provided with a sealable bore in the wall thereof to permit said fluid to be introduced to the well.

4. An apparataus according to claim 1 wherein means are provided for withdrawing fluid from the well.

5. An apparatus according to claim 1 wherein the well is sealed at the mouth by a flexible membrane.

6. An apparatus according to claim 1 wherein said membrane is sealingly connected to the upstanding wall by means of a sealing ring received in an annular recess formed in the wall, the sealing ring sealingly trapping the said membrane.

7. An apparatus according to claim 1 wherein the said membrane is sealingly connected to a part of the moveable housing mounting the trandsucer, by means of a sealing ring.

8. An apparatus according to claim 1 wherein the transducer is mounted in a bore formed in the moveable housing accommodating the transducer, the transducer being sealed by at least one sealing ring mounted between the wall defining the bore and the transducer.

9. An apparatus according to claim 1 wherein the housing accommodating the transducer is mounted on a linear bearings so that the housing, together with the transducer, can move relative to said upstanding wall.

10. An apparatus according to claim 1 wherein an electric motor is provided adapted to drive a threaded rod which passes through a threaded aperture formed in part of the housing accommodating the transducer, actuation of the motor causing rotation of the threaded rod, thus driving the said housing.

11. An apparatus according to claim 1 wherein limit switch means are provided for detecting predetermined limit positions of the housing mounting the transducer.

12. An apparatus according to claim 11 wherein the limit switch means comprise a microswitch co-operating with a cam surface formed or mounted on the movable housing mounting the transducer.

* * * * *